(12) United States Patent
Krajewski et al.

(10) Patent No.: US 8,846,125 B2
(45) Date of Patent: Sep. 30, 2014

(54) ENAMINOCARBONYL COMPOUNDS AND THEIR USE

(75) Inventors: Piotr Krajewski, Warsaw (PL); Agnieszka Woźniak, Warsaw (PL)

(73) Assignee: Instytut Chemii Organicznej, Polska Akademia Nauk, Warsaw (PL)

( * ) Notice: Subject to any disclaimer, the term of this patent is extended or adjusted under 35 U.S.C. 154(b) by 366 days.

(21) Appl. No.: 13/125,598

(22) PCT Filed: Feb. 2, 2010

(86) PCT No.: PCT/PL2010/000010
§ 371 (c)(1),
(2), (4) Date: Jun. 24, 2011

(87) PCT Pub. No.: WO2010/087727
PCT Pub. Date: Aug. 5, 2010

(65) Prior Publication Data
US 2011/0274803 A1    Nov. 10, 2011

(30) Foreign Application Priority Data

Feb. 2, 2009  (PL) ......................................... 387177

(51) Int. Cl.
| | |
|---|---|
| *A23L 1/227* | (2006.01) |
| *C07C 225/18* | (2006.01) |
| *C07D 405/12* | (2006.01) |
| *C07D 307/33* | (2006.01) |
| *A23L 1/226* | (2006.01) |
| *A23L 1/236* | (2006.01) |
| *A23L 1/22* | (2006.01) |
| *C07D 307/58* | (2006.01) |
| *C07C 225/14* | (2006.01) |

(52) U.S. Cl.
CPC ........... *C07D 405/12* (2013.01); *A23L 1/22091* (2013.01); *C07D 307/58* (2013.01); *C07C 225/14* (2013.01); *A23L 1/2369* (2013.01); *A23L 1/236* (2013.01)
USPC ......... 426/548; 549/321; 564/392; 546/284.4

(58) Field of Classification Search
USPC ....................................................... 426/548
See application file for complete search history.

(56) References Cited

U.S. PATENT DOCUMENTS 3,576,009 A * 4/1971 Magnien ..................... 549/321
5,286,509 A * 2/1994 D'Angelo et al. ............ 426/548

OTHER PUBLICATIONS

Hansen, P. E., Bolvig, S., Duus, F., Petrova, M. V., Kawecki, R., Krajewski, R., and Kozerski, L., "Deuterium Isotope Effects on 13C Chemical Shifts of Intramolecularly Hydrogen-Bonded Olefins," Magnetic Resonance in Chemistry, 33:621-631 (1995).*
Krajewski, P., and Kozerski, L., "A Convenient Method for Preparation of Enaminobutryolactones", Synthetic Communications, vol. 34, No. 20, pp. 3737-3742 (2004).*
International Search Report issued by the International Searching Authority (ISA/O.E.P.M. ) on Jun. 30, 2010 in connection with International Application No. PCT/PL2009/000010.
Bassoli A. et al., "A Rational Design of New Intensive Sweeteners From Natural Compounds" , Phytochemical Society of Europe. Annual Proceedings, Oxford University Press, Oxford, GB, Jan. 16, 2000, pp. 27-36.
Kozerski, Lech et al., "17O chemical shifts and deuterium isotope effects on 13C chemical shifts of intramolecularly hydrogen-bonded compounds", Magnetic Resonance in Chemistry, [1998], 36(12), pp. 921-928.
Reddy, D. Srinivasa et al., "Lewis Acid-Mediated Reactions of Alkyl Azides with .alpha.,.beta.-Unsaturated Ketones", Organic Letters, [2003], 5(21), pp. 3899-3902.
Wel H. Van Der et al., "Sweeteners" Food Reviews International, Taylor & Francis, Phildelphia, USA, vol. 3, No. 3, Jan. 1, 1987, p. 193.

* cited by examiner

*Primary Examiner* — Humera Sheikh
*Assistant Examiner* — Jeffrey Mornhinweg
(74) *Attorney, Agent, or Firm* — Gary J. Gershik; Cooper & Dunham LLP

(57) ABSTRACT

The present invention relates to enaminocarbonyl compounds with the formula I. The present invention also relates to the use of compounds with the formula I for the modification of the taste of a product and/or preparation for oral administration.

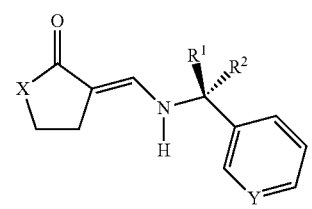

(I)

20 Claims, No Drawings

ENAMINOCARBONYL COMPOUNDS AND THEIR USE

This application is a §371 national stage of PCT International Application No. PCT/PL2010/000010, filed Feb. 2, 2010, designating the United States and claiming priority of Polish Patent Application PL 387 177, filed Feb. 2, 2009, the contents of all of which are hereby incorporated by reference into this application.

The subject of the present invention are enaminocarbonyl compounds, containing a 5-member ring containing a carbonyl group and an enamine group in a side chain attached to a carbon atom adjacent to the carbon atom of the carbonyl group, as well as the use of these compounds as taste modifiers.

In recent times, the number of persons suffering from obesity, hypertension, cardiac and renal disease as well as tooth cavities. These diseases can be caused by the excessive ingestion of saccharose or other caloric sweeteners. Persons afflicted with the abovementioned diseases, diabetics, as well as persons wishing to maintain or decrease their body mass can use artificial sweeteners. The sweeteners impart a sweet taste to the consumed foodstuffs, and at the same time help reduce their calorie content in comparison to products sweetened with ordinary sugar (saccharose) and other caloric sweet substances. Sweeteners are not only used in foodstuffs, but in many other products as well, such as toothpaste, chewing gum, and mouthwash in order to improve their taste (Alternative Sweeteners, 3rd Edition, Revised and Expanded, Lyn O'Brien Nabors Ed., Marcell Dekker, Inc, 2001).

Many low-calorie synthetic sweeteners are known such as acesulfam-K, aspartame, sodium cyclamate, saccharine, or recently sucralose. Despite the fact that a number of the are currently admitted for general marketing in Poland and other nations, a real need still exists to seek out new classes of synthetic compounds which could be used as sweeteners.

International patent application PCT/US2008/055913 discloses protein compounds with a sweet taste. These compounds are analogues of brasein, a protein of 53 amino-acid residues.

International patent application PCT/US2008/063850 discloses sulphamine derivatives with the formula $R_3OS(O)_2$—$NR_1R_2$, where $R_3$ denotes an alkaline or an alkaline earth metal atom, and $R_1$ and/or $R_2$ denotes a an alkyl, cycloalkyl or heterocyclic substituent. Compounds according to that invention exhibit the property of intensifying a sweet taste.

Aside from sweeteners, sweet taste is also modified through the use of sweet taste inhibitors. Many foodstuffs such as jams or fruit jellies contain large quantities of saccharose as a preservative. Moreover, saccharose and other caloric sweeteners are used as fillers and gelling temperature reducers. Inhibitors are used to mitigate the overly sweet taste that lower the perceived sweetness to a desirable level. Furthermore, the inhibitors may be used to improve the taste of artificial sweeteners characterised by a persistent taste or unpleasant aftertaste. A commonly used inhibitor of sweet taste is for example the sodium salt of 2-(4-methoxyphenoxy) propanoic acid (Alternative Sweeteners, 3rd Edition, Revised and Expanded, Lyn O'Brien Nabors, Marcell Dekker, Inc, 2001).

The goal of the present invention is to deliver compounds exhibiting the properties of imparting and enhancing a sweet taste, as well as inhibiting a sweet taste, as well as the use of compounds to modify taste.

A compound according to the present invention is an enaminocarbonyl compound with the formula I

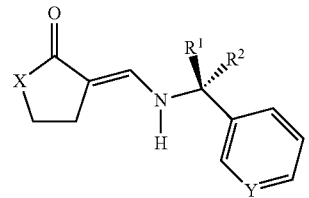

in which
X denotes O or $CH_2$,
Y denotes N and each of $R^1$ and $R^2$ denotes hydrogen,
or Y denotes CH and either one of $R^1$ or $R^2$ denotes a $C_{1-4}$ alkyl, and the remaining $R^1$ or $R^2$ denotes hydrogen,
wherein if Y denotes CH, and at the same time $R^1$ or $R^2$ denotes a $C_{1-4}$ alkyl, then the compound is selected from a group encompassing a mixture of R and S enantiomers enriched in enantiomer R, a mixture of R and S enantiomers enriched in S, enantiomer R and enantiomer S,
in the form of isomer E, and/or isomer Z, and/or a tautomer.

Preferentially, in formula I: X denotes O or $CH_2$, Y denotes CH, one of $R^1$ or $R^2$ denotes a $C_{1-4}$ alkyl, and the remaining $R^1$ or $R^2$ denotes hydrogen, wherein the compound is selected from a group encompassing a mixture of R and S enantiomers containing at least 90% of enantiomer R, preferentially, at least 95% enantiomer R, a mixture of R and S containing at least 90% enantiomer S, preferentially, at least 95% enantiomer S, enantiomer R and enantiomer S,
in the form of isomer E, and/or isomer Z, and/or a tautomer.

Preferentially, in formula I: X denotes O or $CH_2$, Y denotes a CH, one of $R^1$ or $R^2$ is selected from a group encompassing methyl or ethyl, denotes H, and the remaining substituent $R^1$ or $R^2$ denotes hydrogen.

In particular, the compound is (R)-3-(1-phenylethyl)aminomethylenedihydrofuran-2-one.

In particular, the compound is (S)-3-(1-phenylethyl)aminomethylenedihydrofuran-2-one.

In particular, the compound is (R)-3-(1-phenylpropylo) aminomethylenedihydrofuran-2-one.

In particular, the compound is (S)-3-(1-phenylpropylo) aminomethylenedihydrofuran-2-one.

In particular, the compound is (R)-2-(1-phenylethyl)aminomethylenecyclopentanone.

In particular, the compound is (S)-2-(1-phenylethyl)aminomethylenecyclopentanone.

In particular, the compound is 3-(3-pirydylomethyl)aminomethylenedihydrofuran-2-one.

According to the present invention, a compound with the formula I

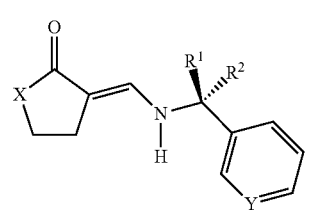

is used, in which X denotes O or CH$_2$, Y denotes a CH, one of R$^1$ or R$^2$ is selected from a group encompassing hydrogen and a C$_{1-4}$ alkyl, and the remaining R$^1$ or R$^2$ denotes hydrogen, wherein if R$^1$ or R$^2$ denotes a C$_{1-4}$ alkyl, to compound is selected from a group encompassing a mixture of R and S enantiomers enriched in enantiomer R, a mixture of R and S enriched in S, enantiomer R and enantiomer S, in the form of isomer E, and/or isomer Z, and/or a tautomer, in the modification of the taste of a product and/or a preparation for oral administration.

Preferentially, a compound with the formula I is used, in which each of R$^1$ and R$^2$ denotes hydrogen, to impart or augment the perception of sweetness of a product and/or preparation for oral administration.

In particular, the compound used is 3-benzylaminomethylenedihydrofuran-2-one.

In particular, the compound used is 2-benzylaminomethylenecyclopentanone.

Preferentially, the compound with the formula I, in which one of R$^1$ or R$^2$ denotes a C$_{1-4}$ alkyl, and the remaining R$^1$ or R$^2$ denotes hydrogen, which compound is selected from a group encompassing a mixture of R and S enantiomers enriched in enantiomer R and encompassing enantiomer R, is used in the modification of the taste of a product and/or a preparation for oral administration.

In particular, the compound used is (R)-3-(1-phenylethyl)aminomethylenedihydrofuran-2-one.

In particular, the compound used is (R)-3-(1-phenylpropylo)aminomethylenedihydrofuran-2-one.

In particular, the compound used is (R)-2-(1-phenylethyl)aminomethylenecyclopentanone.

Preferentially, the compound with the formula I, in which one of R$^1$ or R$^2$ denotes a C$_{1-4}$ alkyl, and the remaining R$^1$ or R$^2$ denotes hydrogen, which compound is selected from a group encompassing a mixture of R and S enantiomers enriched in enantiomer S and encompassing enantiomer S, is used to inhibit the perception of sweetness of a product and/or a preparation for oral administration.

In particular, the compound used is (S)-3-(1-phenylethyl)aminomethylenedihydrofuran-2-one.

In particular, the compound used is (S)-3-(1-phenylpropylo)aminomethylenedihydrofuran-2-one.

In particular, the compound used is (S)-2-(1-phenylethyl)aminomethylenecyclopentanone.

Compounds according to the present invention are produced using an efficient, two-stage synthesis from inexpensive, available raw materials. A defined group of compounds according to the present invention, encompassing achiral and chiral compounds of the R configuration, exhibit the property of imparting and enhancing a sweet taste, wherein these compounds are characterised by a beneficial taste profile. Compounds from this group with the opposite chirality, meaning chiral compounds according with the S configuration, exhibit the property of inhibiting sweet taste. Due to the structural analogy of compounds imparting the perception of sweet taste and those inhibiting the perception of sweet taste, it is possible to use these compounds in research on the relationship between chemical structure and sweet taste imparting/inhibiting properties.

Compounds according to the present invention are compounds with the formula I

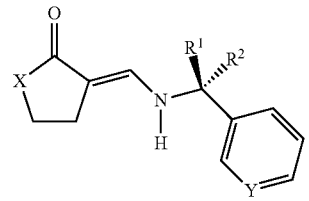

(I)

in which
X denotes O or CH$_2$,
Y denotes N and each of R$^1$ and R$^2$ denotes hydrogen,
or Y denotes a CH and either R$^1$ or R$^2$ is selected from a group encompassing hydrogen and a C$_{1-4}$ alkyl, and the remaining R$^1$ or R$^2$ denotes hydrogen,
with the exclusion of the following compounds:
3-benzylaminomethylenedihydrofuran-2-one,
2-benzylaminomethylcyclopentanone,
wherein if Y denotes a CH and R$^1$ or R$^2$ denotes a C$_{1-4}$ alkyl then the compound is selected from a group encompassing a mixture of R and S enantiomers enriched in enantiomer R, a mixture of R and S enriched in enantiomer S, and enantiomer R and enantiomer S.

3-Benzylaminomethylenedihydrofuran-2-one is a known compound (see: L. Kozerski et al., Magn. Reson. Chem., 1998, 36(12), 921-928; P. Krajewski et al., Synth. Commun. 34(20), 2004, 3737-3742). No data is available in literature regarding the utilitarian properties of the se compounds in terms of taste modification.

2-Benzylaminomethylcyclopentanone is a known compound (see: N. B. Marczenko et al., Khim. Geterotsikl. Soedin., 1982, 1, 68-71). No data is available in literature regarding the utilitarian properties of the se compounds in terms of taste modification.

If one of R$^1$ or R$^2$ denotes a C$_{1-4}$ alkyl, and the remaining R$^1$ or R$^2$ denotes hydrogen, then the compound with the formula I contains an asymmetric carbon atom (indicated in formula IA with an asterisk)

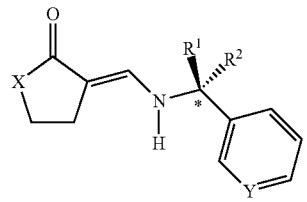

(IA)

and then the compound denoted with formula I can occur in the form of a racemic mixture, a mixture of R and S enantiomers enriched in enantiomer R, in the form of a mixture of R and S enantiomers enriched in enantiomer S, in the form of enantiomer R or in the form of enantiomer S. As indicated above, compounds according to the present invention are also compounds with the formula I, which (if they contain an asymmetric carbon atom) are selected from a group encompassing enantiomer R, enantiomer S as well as a mixture of R and S enantiomers enriched in enantiomer R and a mixture of R and S enriched in enantiomer S.

Unexpectedly, it was observed that compounds according to the present invention exhibit taste-modifying properties. Compounds with the formula I, in which X denotes O or CH$_2$, Y denotes N or CH, and R$^1$ and R$^2$ denote hydrogen, exhibit the property of imparting and enhancing the perception of a sweet taste. Compounds with the formula I according to the present invention, in which one of $R^1$ or $R^2$ is selected from a group encompassing hydrogen and a $C_{1-4}$ alkyl, and the remaining $R^1$ and $R^2$ denotes hydrogen, also exhibit the property of imparting and enhancing a sweet, if the configuration of the carbon bound to substituents $R^1$ and $R^2$ is R. However, compounds according to the present invention, in which either $R^1$ or $R^2$ is selected from a group encompassing hydrogen and a $C_{1-4}$ alkyl, and the remaining $R^1$ or $R^2$ denotes hydrogen, wherein the configuration of the carbon bound to substituents $R^1$ and $R^2$ is S, exhibit the property of inhibiting sweet taste.

This particular and opposite taste-modifying activity induced by the R and S enantiomers results in that a racemic mixture of the compound with the formula I, in which there is a chiral carbon atom bound with substituents $R^1$ and $R^2$, and which contains 50% enantiomer R and 50% enantiomer S, does not exhibit a sweet taste. However, a mixture enriched in one of the enantiomers, R or S, exhibits a useful property characteristic of the enantiomer present in the greater quantity, and the degree of the intensity this property is dependent on the degree of enrichment of the mixture in terms of this enantiomer.

Due to the presence of the carbonyl group and the enamine group bound to the carbon adjacent to the carbon atom with the carbonyl group, compounds with the formula I belong to the group of compounds known as "push-pull ethylenes", meaning compounds possessing a strongly polarised double carbon-carbon bond. (see: J. Sandström Top. Stereochem. 14, 1983, 83). The energetic barrier to rotation about the double bond is greatly reduced, in comparison with compounds containing a non-polarised carbon-carbon double bond, for which isomerisation, isomer Z→isomer E and/or isomer E→isomer Z, is not observed under normal and close to normal conditions. In contrast to typical Z/E isomers (or cis/trans), compounds with the formula I can isomerise in solution at ambient temperature. In non-polar and moderately polar solvents, and in mixtures thereof, compounds with the formula I can occur in the form of a mixture of Z and E. In polar solvents such as DMSO, alcohols, water and pyridine the equilibrium between Z and E can be entirely shifted towards isomer E. In a crystalline state, compounds with the formula I usually occur in the form of isomer E.

Independently of the possibility of the occurrence of isomers Z/E and isomerisation (isomer Z→isomer E and/or isomer E→isomer Z), compounds with the formula I can occur in the form of a series of tautomers, whose structures are shown in Diagram I.

Diagram I

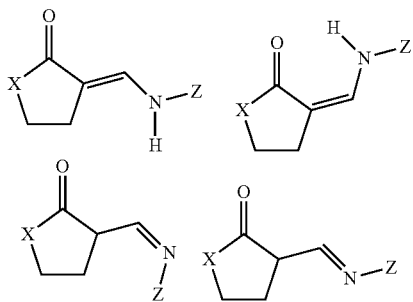

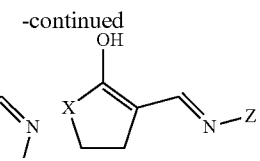

If in formula I: X denotes a $CH_2$, then the compound with the formula I can also occur in the tautomeric forms shown in Diagram II.

Diagram II

The term "enaminocarbonyl compound" within the meaning of the description and claims of the present invention encompasses a compound with the formula I in the form of isomer E, in the form of isomer Z, in the form of a mixture of isomers E and Z, as well as the tautomeric form shown in Diagram I and/or II, wherein if the carbon atom directly bound to substituents $R^1$ and $R^2$ is an asymmetric atom, then this also encompasses a compound with the formula I in the form of a mixture of R and S enantiomers enriched in enantiomer R, in the form of a mixture of R and S enantiomers enriched in enantiomer S, in the form of enantiomer R or in the form of enantiomer S.

The term "taste-modifying compound" within the meaning the description and claims of the present invention denotes a compound with the formula I, which is characterised by the property of modifying the perception of sweetness upon oral administration, In particular, the property of imparting or enhancing a sweet taste or the property of inhibiting the sweet taste of substances and/or products characterised by a sweet taste, or mixtures of substances and/or products characterised by a sweet taste.

Enaminocarbonyl compounds are usually produced from 1,3-dicarbonyl compounds and appropriate amines (J. V. Greenhill, J. Chem. Soc. Rev., 6, 1977, 277-294).

Enaminocarbonyl compounds, such as enaminobutyryl lactones (compounds with the formula I, in which X denotes O) can be produced using several methods described in literature. For example a method is known of producing 3-dimethylaminomethylenedihydrofuran-2-one through the condensation of 4-butyryl lactone with dimethylacetal dimethylformamide (DMA-DMF), and then the transamination of the enaminolactone produced using an appropriate free primary amine (N. B. Marczenko et al., Khim. Geterotsikl. Soedin., 1982, 1, 68-71). Moreover, 3-benzylaminomethylenedihydrofuran-2-one can be produced through the condensation of benzylamine and 2-oxo-cyclopentanocarbaldehyde (A. Missoum et al., Synth. Commun., 27(3), 1997, 453-466). According to another known method, 4-butyryl lactone is condensed with methyl or methyl formate in the presence of one equivalent of sodium hydride. During the initial stage, a 3-hydroxymethylenedihydrofuran-2-one sodium salt is produced which, during the second stage, is condensed with a primary amine in the form of an additive salt, in the presence of methanol as a solvent (P. Krajewski et al., Synth. Commun., 34(20), 2004, 3737-3742).

Enaminocarbonyl compounds, such as enaminocyclopentanones (compounds with the formula I, in which X denotes a $CH_2$) are produced using a the method using DMA-DMF, condensing the cyclopentanone with DMA-DMF, whereafter the 2-dimethylaminomethylenecyclopentanone is transaminated using an appropriate free amine. Enaminocyclopentanones are also produced through a reaction of cyclohex-2-enone with alkyl azides in the presence of Lewis acid (D. Srinivassa Reddy et al., Org. Lett., 5(21) 2003, 3899-3903).

In one embodiment, compounds with the formula I, in which X denotes O, Y denotes N and each of $R^1$ and $R^2$ denotes hydrogen, or Y denotes a CH and either $R^1$ or $R^2$ is selected from a group encompassing hydrogen and a $C_{1-4}$ alkyl, and the remaining $R^1$ or $R^2$ denotes hydrogen, are produced through the reaction shown in Diagram III.

Diagram III

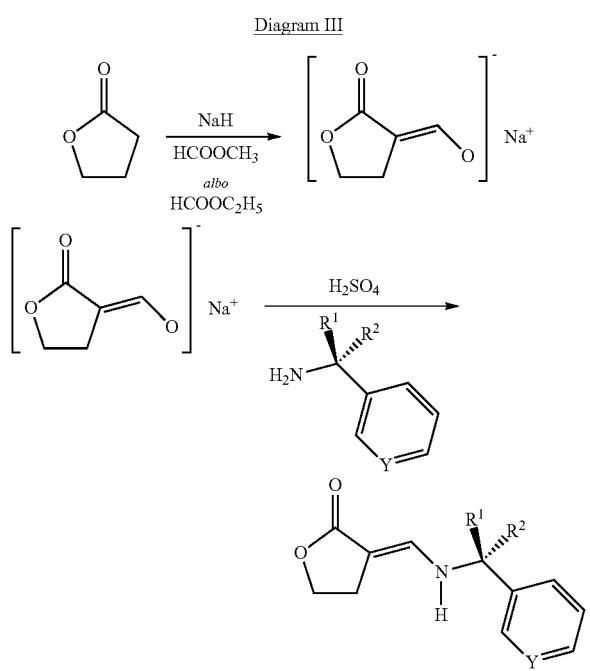

In another embodiment, compounds with the formula I, in which X denotes O, Y denotes N and each of $R^1$ and $R^2$ denotes hydrogen, or Y denotes a CH and either $R^1$ or $R^2$ is selected from a group encompassing hydrogen and a $C_{1-4}$ alkyl, and the remaining $R^1$ or $R^2$ denotes hydrogen, are produced in a reaction shown in Diagram IV.

Diagram IV

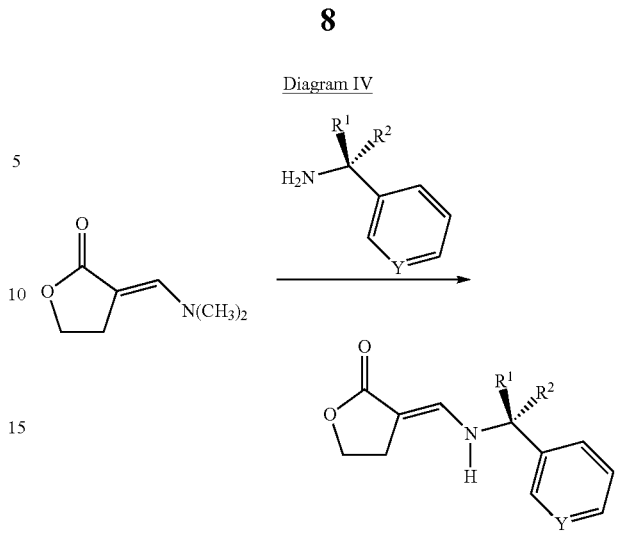

In another embodiment, compounds with the formula I, in which X denotes a $CH_2$, Y denotes a CH and either $R^1$ or $R^2$ is selected from a group encompassing hydrogen and a $C_{1-4}$ alkyl and the remaining $R^1$ or $R^2$ denotes hydrogen, are produced in a reaction shown in Diagram V.

Diagram V

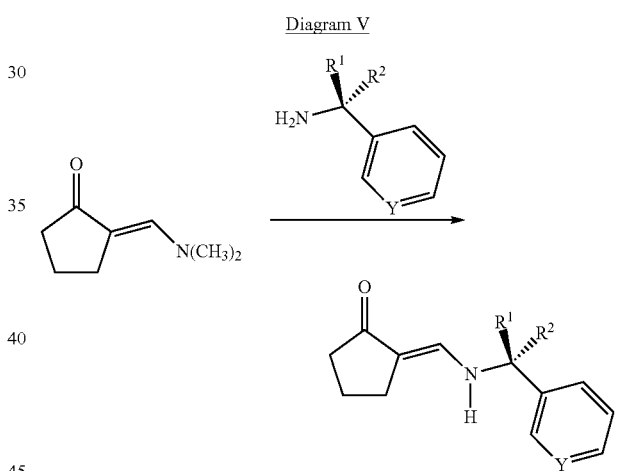

The present invention is illustrated by the following examples, which do not limit the scope of the present invention.

EXAMPLES

We used the following general methods A1, A2 and B to produce compounds with the formula I in which X denotes O, whereas in order to produce compounds with the formula I in which X denotes a CH, we used a procedure according to method C.

In order to produce compounds according to the present invention, we used amines with the formula $H_2NC(R^1R^2)Ar$ (where Ar denotes phenyl or 3-pirydyl, and $R^1$ or $R^2$ denotes H or a $C_{1-4}$alkyl), or possibly their additive salts with acids. If $R^1$ or $R^2$ denotes a $C_{1-4}$ alkyl, then the amine $H_2NC*(R^1R^2)Ar$ contains an asymmetric carbon atom (indicated with an asterisk) and can occur in the form of a racemic mixture, a mixture of R and S enantiomers enriched in enantiomer R, in the form of a mixture of R and S enantiomers enriched in enantiomer S, in the form of enantiomer R or in the form of enantiomer S.

The examples below make use of commercially available chiral R or S amines with an enantiomeric excess of 96% (meaning an optical purity of ca. 98%). Comparative examples also make use of amines with the formula $H_2NC(R^1R^2)Ar$ in the form of racemic mixtures as well as amines with the formulae $H_2NAlkyl$ and $H_2NAryl$.

The 3-hydroxymethylenedihydrofuran-2-one sodium salt, used as the raw material in methods A1 and A2, is produced according to the following procedure. A round-bottomed flask equipped with a magnetic stirrer and a flow-through cooler is loaded with sodium hydride (0.5 moles, 50% suspension in mineral oil) and hexane (500 ml). A mixture of 4-butyryl lactone (0.5 moles) and alkyl formate (0.5 moles; the alkyl is methyl or ethyl) is then added dropwise into the flask. After dripping in 10% of the mixture volume, 3 ml of ethanol are added into the flask to initiate the reaction. The reaction mixture is maintained at boiling temperature for 2 hours, then cooled, and the sodium salt produced is filtered, washed with hexane and dried under reduced pressure.

Method A1

3-hydroxymethylenedihydrofuran-2-one sodium salt (50 mmol) is placed in a round-bottomed flask equipped with a magnetic stirrer and 20 ml of distilled water are added. The contents are mixed for several minutes until dissolution. Next, the free amine is added (55 mmol) and concentrated sulphuric acid is added dropwise (2 ml), at such a rate so as to maintain the temperature below 30° C. The precipitated enaminocarbonyl compound is filtered, washed with distilled water and air-dried. Alternatively, instead of the free amine, one can use an additive sale of the amine with the acid, preferentially an inorganic one, such as an amine hydrochloride.

Method A2

3-hydroxymethylenedihydrofuran-2-one sodium salt (10 mmol) is placed in a round-bottomed flask equipped with a magnetic stirrer and 5 ml of distilled water are added at room temperature. The contents are mixed for several minutes until dissolution. Next, the free amine is added (11 mmol) and concentrated sulphuric acid is added dropwise (0.4 ml), at such a rate so as to maintain the temperature below 30° C. The precipitated enaminocarbonyl compound is filtered, washed with distilled water and air-dried.

Method B

3-Dimethylaminomethylenedihydrofuran-2-one (10 mmol) and a free amine (10 mmol) are placed in a round-bottomed flask equipped with a magnetic stirrer and a flow-through cooler and heated to boiling for 60 minutes. The mixture is then cooled and left until the oily phase separates, which solidifies during storage. The raw product is broken up, washed with diethyl ether and crystallised out of aqueous ethanol.

Method C

2-Dimethylaminomethylenecyclopentanone (50 mmol) and a free amine (50 mmol) are placed in a round-bottomed flask equipped with a magnetic stirrer and a flow-through cooler and heated to boiling for 60 minutes. The mixture is then cooled and left until the oily phase separates, which solidifies during storage. The raw product is broken up, washed with diethyl ether and crystallised out of aqueous ethanol.

Example 1

3-Benzylaminomethylenedihydrofuran-2-one

Using 3-hydroxymethylenedihydrofuran-2-one sodium salt (50 mmol) and benzylamine (55 mmol) and using the abovementioned method A1, 3-benzylaminomethylenedihydrofuran-2-one is produced (7.50 g, efficiency: 70%) in the form of a white powder.

Alternatively, using the abovementioned method B and using 3-dimethylaminomethylenedihydrofuran-2-one (10 mmol) and benzylamine (10 mmol), 3-benzylaminomethylenedihydrofuran-2-one (1.80 g, efficiency: 89%) is produced in the form of a pale yellow powder.

Spectral data:
$^1H$ NMR (400 MHz, $CD_3SOCD_3$, 25° C., isomer E), δ: 2.65 (t, J=7.6 Hz, 2H, 4-$CH_2$), 4.16 (t, J=7.6 Hz, 2H, 5-$CH_2$), 4.34 (d, J=5.1 Hz, 2H, $NCH_2$), 7.1-7.4 (m, 7H, =CH, NH, phenyl).

Example 2

(R)-3-(1-phenylethyl)aminomethylenedihydrofuran-2-one

Using 3-hydroxymethylenedihydrofuran-2-one sodium salt (50 mmol) and (R)-1-phenylethylamine (55 mmol) and proceeding according to the abovementioned method A1, (R)-3-(1-phenylethylamino)methylenedihydrofuran-2-one (7.70 g, efficiency: 71%) is produced in the form of a white powder.

Spectral data:
$^1H$ NMR (400 MHz, $CD_3SOCD_3$, 25° C., isomer E), δ: 1.43 (d, J=6.9 Hz, 3H, $CH_3$), 2.67 (t, J=7.5 Hz, 2H, 4-$CH_2$), 4.15 (t, J=7.5 Hz, 2H, 5-$CH_2$), 4.55 (m, 1H, NCH), 7.0-7.5 (m, 7H, =CH, NH, phenyl).

Example 3

(S)-3-(1-phenylethyl)aminomethylenedihydrofuran-2-one

Using 3-hydroxymethylenedihydrofuran-2-one sodium salt (50 mmol) and (S)-1-phenylethylamine (55 mmol) and proceeding according to the abovementioned method A1, (S)-3-(1-phenylethylamino)methylenedihydrofuran-2-one (7.92 g, efficiency: 73%) is produced in the form of a white powder.

Spectral data:
$^1H$ NMR (400 MHz, $CD_3SOCD_3$, 25° C., isomer K), δ: 1.43 (d, J=6.9 Hz, 3H, $CH_3$), 2.67 (t, J=7.5 Hz, 2H, 4-$CH_2$), 4.15 (t, J=7.5 Hz, 2H, 5-$CH_2$), 4.55 (m, 1H, NCH), 7.0-7.5 (m, 7H, =CH, NH, phenyl).

Example 4

(R)-3-(1-phenylpropylo)aminomethylenedihydrofuran-2-one

Using 3-dimethylaminomethylenedihydrofuran-2-one (10 mmol) and (R)-1-phenylpropyloamine (10 mmol) and proceeding according to the abovementioned method B, (R)-3-(1-phenylethylamino)methylenedihydrofuran-2-one (1.40 g, efficiency: 65%) is produced in the form of a white powder.

Spectral data:
$^1H$ NMR (400 MHz, $CD_3SOCD_3$, 25° C., isomer E), δ: 0.86 (t, 3H), 1.74-1.82 (m, 2H), 2.70 (bt, 2H), 4.15 (t, 2H), 4.55 (m, 1H, NCH), 4.24 (m, 1H), 7.11-7.34 (m, 7H).

Example 5

(S)-3-(1-phenylpropylo)aminomethylenedihydrofuran-2-one

Using 3-dimethylaminomethylenedihydrofuran-2-one (10 mmol) and (S)-1-phenylpropyloamine (10 mmol) and proceeding according to the abovementioned method B, (S)-3-(1-phenylethylamino)methylenedihydrofuran-2-one (1.46 g, efficiency: 68%) is produced in the form of a white powder.

Spectral data:
$^1$H NMR (400 MHz, CD$_3$SOCD$_3$, 25° C., isomer E), δ: 0.86 (t, 3H), 1.74-1.82 (m, 2H), 2.70 (bt, 2H), 4.15 (t, 2H), 4.55 (m, 1H, NCH), 4.24 (m, 1H), 7.11-7.34 (m, 7H).

Example 6

2-Benzylaminomethylenecyclopentanone

Using 2-dimethylaminomethylenecyclopentanone (50 mmol) and benzylamine (50 mmol) and proceeding according to the abovementioned method C, 2-benzylaminomethylenecyclopentanone (7.4 g, efficiency: 70%) is produced in the form of a pale yellow powder.

Spectral data:
$^1$H NMR (400 MHz, CD$_3$SOCD$_3$, 25° C., mixture of isomers E and Z), δ: 1.70-1.80 (m, 2H, CH$_2$, E and Z), 2.03 (t, 2H, CH$_2$, E), 2.15 (t, 2H, CH$_2$, Z), 2.36 (t, 2H, CH$_2$, E), 2.42 (t, 2H, CH$_2$, Z), 4.40 (d, 2H, CH$_2$N, E and Z), 7.14-7.36 (m, 6H, =CH, phenyl, E and Z).

Example 7

(R)-2-(1-phenylethyl)aminomethylenecyclopentanone

Using 2-dimethylaminomethylenecyclopentanone (50 mmol) and (R)-1-phenylethylamine (50 mmol) and proceeding according to the abovementioned method C, (R)-3-(1-phenylethylamino)methylenedihydrofuran-2-one (7.3 g, efficiency: 65%) is produced in the form of a pale yellow powder.

Spectral data:
$^1$H NMR (400 MHz, CD$_3$SOCD$_3$, 25° C., mixture of isomers E and Z), δ: 1.45 (d, 3H, CH$_3$, E and Z), 1.68-1.82 (m, 2H, CH$_2$, E and Z), 1.97-2.17 (m, 2H, CH$_2$, E and Z), 2.31-2.45 (m, 2H, CH$_2$, E and Z), 4.60 (m, 1H, CHN, E and Z), 7.05-7.42 (m, 7H, =CH, NH, phenyl, E and Z).

Example 8

(S)-2-(1-phenylethyl)aminomethylenecyclopentanone

Using 2-dimethylaminomethylenecyclopentanone (50 mmol) and (S)-1-phenylethylamine (50 mmol) and proceeding according to the abovementioned method C, (S)-3-(1-phenylethylamino)methylenedihydrofuran-2-one (7.7 g, efficiency: 69%) is produced in the form of a pale yellow powder.

Spectral data:
$^1$H NMR (400 MHz, CD$_3$SOCD$_3$, 25° C., mixture of isomers E and Z), δ: 1.45 (d, 3H, CH$_3$, E and Z), 1.68-1.82 (m, 2H, CH$_2$, E and Z), 1.97-2.17 (m, 2H, CH$_2$, E and Z), 2.31-2.45 (m, 2H, CH$_2$, E and Z), 4.60 (m, 1H, CHN, E and Z), 7.05-7.42 (m, 7H, =CH, NH, phenyl, E and Z).

Example 9

3-(3-pirydylomethyl)aminomethylenedihydrofuran-2-one

Using 3-hydroxymethylenedihydrofuran-2-one sodium salt (10 mmol) and 3-pirydylomethylamine (10 mmol) and proceeding according to the abovementioned method A2, 3-(3-pirydylomethyl)aminomethylenedihydrofuran-2-one (0.71 g, efficiency: 35%) is produced in the form of a white powder.

Spectral data:
$^1$H NMR (400 MHz, CD$_3$SOCD$_3$, 25° C., isomer E), δ: 2.64 (t, J=7.7 Hz, 2H), 4.16 (t, J=7.7 Hz, 2H), 4.37 (d, J=4.7 Hz, 2H), 7.21 (m, 2H), 7.38 (dd, 1H), 7.67 (bd, J=7.9 Hz, 1H), 8.47 (m, 2H).

COMPARATIVE EXAMPLES

Comparative Example 1

(RS)-3-(1-phenylethyl)aminomethylenedihydrofuran-2-one

Using 3-hydroxymethylenedihydrofuran-2-one sodium salt (50 mmol) and racemic (R,S)-1-phenylethylamine (55 mmol) and proceeding according to the abovementioned method A1, (R,S)-3-(1-phenylethylamino)methylenedihydrofuran-2-one (7.70 g, efficiency: 71%) is produced in the form of a white powder.

Spectral data:
$^1$H NMR (400 MHz, CD$_3$SOCD$_3$, 25° C., isomer E), δ: 1.43 (d, J=6.9 Hz, 3H, CH$_3$), 2.67 (t, J=7.5 Hz, 2H, 4-CH$_2$), 4.15 (t, J=7.5 Hz, 2H, 5-CH$_2$), 4.55 (m, 1H, NCH), 7.0-7.5 (m, 7H, =CH, NH, phenyl).

Comparative Example 2

3-(2-phenylethyl)aminomethylenedihydrofuran-2-one

Using 3-hydroxymethylenedihydrofuran-2-one sodium salt (50 mmol) and 2-phenylethylamine (55 mmol) and proceeding according to the abovementioned method A1, 3-(2-phenylethylamino)methylenedihydrofuran-2-one (8.14 g, efficiency: 75%) is produced in the form of a white powder.

Spectral data:
$^1$H NMR (500 MHz, CD$_3$SOCD$_3$, 30° C., isomer E), δ: 2.61 (bs, 2H, CH$_2$), 2.76 (t, J=7.5 Hz, 2H, 4-CH$_2$), 3.37 (m, superimposition with signals HDO, 2H, NCH$_2$), 4.14 (t, J=7.5 Hz, 2H, 5-CH$_2$), 6.85 (m, 1H, NH), 7.08 (d, J=13.3 Hz, 1H, =CH), 7.17-7.30 (m, 5H, phenyl).

Comparative Example 3

3-(2-chlorobenzyl)aminomethylenedihydrofuran-2-one

Using 3-hydroxymethylenedihydrofuran-2-one sodium salt (10 mmol) and 2-chlorobenzylamine (11 mmol) and proceeding according to the abovementioned method A2, 3-(2-chlorobenzylamino)methylenedihydrofuran-2-one (1.54 g, efficiency: 75%) is produced in the form of a white powder.

Spectral data:
$^1$H NMR (500 MHz, CD$_3$SOCD$_3$, 30° C., isomer E), δ: 2.68 (t, J=7.7 Hz, 2H, 4-CH$_2$), 4.17 (t, J=7.7 Hz, 2H, 5-CH$_2$), 4.44 (m, 2H, NCH$_2$), 7.18-7.47 (m, 6H, NH, =CH, aromatic protons).

Comparative Example 4

3-(4-chlorobenzyl)aminomethylenedihydrofuran-2-one

Using 3-hydroxymethylenedihydrofuran-2-one sodium salt (10 mmol) and 4-chlorobenzylamine (11 mmol) and proceeding according to the abovementioned method A2, 3-(4-chlorobenzylamino)methylenedihydrofuran-2-one (1.5 g, 73%) is produced in the form of a white powder.

Spectral data:
$^1$H NMR (500 MHz, CD$_3$SOCD$_3$, 30° C., isomer E), δ: 2.65 (t, J=7.5 Hz, 2H, 4-CH$_2$), 4.16 (t, J=7.5 Hz, 2H, 5-CH$_2$), 4.34 (d, J=5.5 Hz, 2H, NCH$_2$), 7.17-7.26 (m, 2H, NH, =CH), 7.25 and 7.41 (AA'BB', 4H, aromatic protons).

Comparative Example 5

3-(4-methoxybenzyl)aminomethylenedihydrofuran-2-one

Using 3-hydroxymethylenedihydrofuran-2-one sodium salt (50 mmol) and 4-methoxybenzylamine (55 mmol) and proceeding according to the abovementioned method A1, 3-(4-methoxybenzylamino)methylenedihydrofuran-2-one (2.9 g, efficiency: 28%) is produced in the form of a white powder.
Spectral data:
$^1$H NMR (500 MHz, CD$_3$SOCD$_3$, 30° C., isomer E), δ: 2.64 (bt, J=7.1 Hz, 2H, 4-CH$_2$), 3.73 (s, 3H, OCH$_3$), 4.15 (t, J=7.6 Hz, 2H, 5-CH$_2$), 4.26 (d, J=5.0 Hz, 2H, NCH$_2$), 6.90 (d, J=8.6 Hz, 2H, aromatic protons), 7.14-7.22 (m, 4H, =CH, NH, aromatic protons).

Comparative Example 6

3-(2-pirydylomethyl)aminomethylenedihydrofuran-2-one

Using 3-hydroxymethylenedihydrofuran-2-one sodium salt (10 mmol) and 2-pirydylomethylamine (11 mmol) and proceeding according to the abovementioned method A2, 3-(2-pirydylomethyl)aminomethylenedihydrofuran-2-one (0.8 g, 39%) is produced in the form of a white powder.
Spectral data:
$^1$H-NMR (500 MHz, CD$_3$SOCD$_3$, 30° C.), δ: 2.66 (t, J=7.5 Hz, 2H, 4-CH$_2$), 4.17 (t, J=7.6 Hz, 2-H, 5-CH$_2$), 4.42 (d, J=5.6 Hz, 2H, NCH$_2$), 7.32-7.19 (m, 4H, =CH, NH, two aromatic protons), 7.78 (td, J=6.2 Hz, 1H, aromatic proton), 8.52 (d, J=4.7 Hz, 1H, aromatic proton).

Comparative Example 7

3-benzylaminomethylenetetrahydropiran-2-one

Using 3-hydroxymethylenedihydropiran-2-one sodium salt (50 mmol) and benzylamine (55 mmol) and proceeding according to the abovementioned method A1, 3-benzylaminomethylenetetrahydropiran-2-one (3.91 g, efficiency: 69%) is produced in the form of a white powder.
Spectral data:
$^1$H NMR (400 MHz, CD$_3$SOCD$_3$, 25° C., isomer E), δ: 1.74 (m, 2H, 5-CH$_2$), 2.20 (td, J=7.6 Hz, 2H, 4-CH$_2$), 4.06 (t, J=5.2 Hz, 2H, 6-CH$_2$), 4.35 (d, J=5.9 Hz, 2H, NCH$_2$), 7.14-7.34 (m, 6H, NH, aromatic protons), 7.46 (dt, J=14.0 Hz, J=1.5 Hz, 1H, =CH).

Comparative Examples 8-11

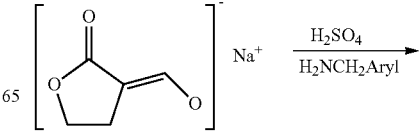

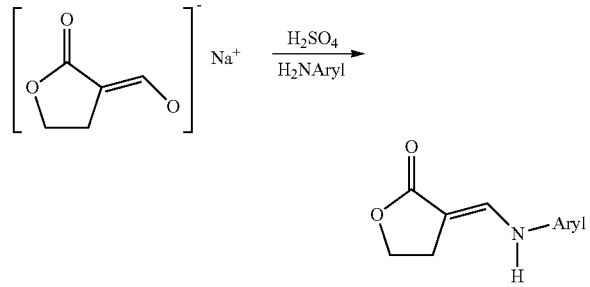

Using 3-hydroxymethylenedihydrofuran-2-one sodium salt (10 mmol) and a primary amine (11 mmol) with the formula H$_2$NAlkyl (where Alkyl denotes methyl, i-propyl, ethyl or tert-butyl) and proceeding according to the abovementioned method A2, the following compounds were produced:

| Comparative example No. | Resulting furan-2-one compound |
|---|---|
| 8 | 3-methylaminomethylenedihydrofuran-2-one |
| 9 | 3-(2-propylo)aminomethylenedihydrofuran-2-one |
| 10 | 3-ethylaminomethylenedihydrofuran-2-one |
| 11 | 3-tert-butylaminomethylenedihydrofuran-2-one |

Comparative Examples 12-16

Using 3-hydroxymethylenedihydrofuran-2-one sodium salt (10 mmol) and a primary amine (11 mmol) with the formula H$_2$NAr (where Ar denotes phenyl, 2-methylphenyl, 3-nitrophenyl, 4-hydroxyphenyl, 4-methoxyphenyl) and proceeding according to the abovementioned method A2, the following compounds were produced:

| Comparative example No. | Resulting furan-2-one compound |
|---|---|
| 12 | phenylaminomethylenedihydrofuran-2-one |
| 13 | 3-(2-methylphenyl)aminomethylenedihydrofuran-2-one |
| 14 | 3-(3-nitrophenyl)aminomethylenedihydrofuran-2-one |
| 15 | 3-(4-hydroxyphenyl)aminomethylenedihydrofuran-2-one |
| 16 | 3-(4-methoxyphenyl)aminomethylenedihydrofuran-2-one |

Comparative Examples 17-19

-continued

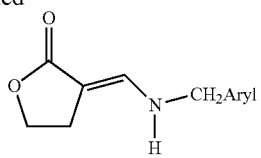

Using 3-hydroxymethylenedihydrofuran-2-one sodium salt (10 mmol) and a primary amine (11 mmol) with the formula H$_2$NCH$_2$Aryl (where Aryl denotes 4-hydroxyphenyl, 2-naftyl, 2-furyl) and proceeding according to the abovementioned method A2, the following compounds were produced:

| Comparative example No. | Resulting furan-2-one compound |
|---|---|
| 17 | 3-(4-hydroxybenzyl)aminomethylenedihydrofuran-2-one |
| 18 | 3-(2-naftylomethyl)aminomethylenedihydrofuran-2-one |
| 19 | 3-(2-furylomethyl)aminomethylenedihydrofuran-2-one |

Evaluation of the taste-modifying properties of compounds according to the present invention Compounds according to the present invention destined for testing of their taste perception modifying properties were re-crystallized from ethanol or an ethanol-water mixture.

Qualitative evaluation of the perception of sweet taste; the examined substances were dissolved in a 20% ethanol and water mixture (vol./vol.).

Three initial solutions were formulated, containing:
the compound of example 1 (3-benzylaminomethylenedihydrofuran-2-one, 4000 ppm solution-400 mg in 100 ml 20% ethanol),
compound of example 2 ((R)-3-(1-phenylethylamino)methylenedihydrofuran-2-one, 4000 ppm solution-400 mg in 100 ml 20% ethanol),
compound of example 6 (2-benzylaminomethylenecyclopentanone, 4000 ppm solution–400 mg in 100 ml 20% ethanol).

Solutions of lower concentrations were obtained through dilution, to appropriate proportions, of the initial solutions with a 20% mixture of ethanol and distilled water (vol./vol.).

Evaluation of the degree of sweetness of the compounds according to the present invention was performed using a 5-volunteer panel—healthy men—henceforth referred to as panel members. All panel members were informed of the need to maintain safety procedures during the evaluation of the compounds according to the present invention, In particular, of the need to avoid swallowing the tested solutions. Each of the panel members received a 10 ml sample of a solution in a small vial and rinsed out his mouth with the entire contents of the vial for 20 seconds and then spit out the tested solution. Next, he carefully rinsed out his mouth with a large volume of distilled water (at least 150 ml) for at least 30 seconds. When the panel member felt that he no longer perceived any taste, he could proceed with the evaluation of the next solution.

During the first stage, the panel members qualitatively examined the taste of the three initial solutions containing 4000 ppm of a compound according to the present invention. The panel members all agreed that the solutions have an intensive sweet taste.

An additional qualitative evaluation was made of compounds according to the present invention from examples 4, 7 and 9, and compounds from comparative examples 1-19, in the form of 4000 ppm solutions. The solutions of compounds from examples 4 and 7 also have an intensively sweet taste, whereas the solution of example 9 (3-(3-pirydylomethylamino)methylenedihydrofuran-2-one) was described by the panel members as significantly less sweet than the solution of 3-benzylaminomethylenedihydrofuran-2-one (compound of example 1) of the same concentration, moreover with an admixture of a bitter taste. Solutions of compounds from the comparative examples lack a sweet taste. The results of the evaluation are shown in Table 1 below.

TABLE 1

| Compound according to the present invention, (according to example) | Perception of sweet taste [a, b, c] |
|---|---|
| 1 | ++ |
| 2 | ++ |
| 4 | ++ |
| 6 | ++ |
| 7 | ++ |
| 9 | + (somewhat bitter) |
| Comparative examples 1-19 | − |

[a] [+] perception of sweet taste,
[b] [++] very strong perception of sweet taste,
[c] [−] absence of sweet taste.

During the next stage, we performed a comparative analysis of the intensity of the sweet taste. In the study we used the compound of example 1 (3-benzyl-aminomethylenedihydrofuran-2-one). The subject of the study consisted of samples of the initial 4000 ppm solution, and samples of diluted solutions containing 2000, 1000, 800 and 500 ppm of the compound of example 1.

The reference solution comprised 10% saccharose (wt./wt.) in 20% ethanol, containing 100000 ppm (wt./wt.) saccharose.

The study operator gave the panel members samples of the compound with the formula 1 marked with randomly generated 3-digit numbers, and also samples of the reference solution of saccharose in order to compare the perception of sweetness to the saccharose reference solution. Each of the 5 panel members received for comparison random samples of the solutions of the compound of example 1, twice, containing 4000 ppm, 2000 ppm, 1000 ppm, 800 ppm and 500 ppm of the compound. Each concentration was thus examined in 10 comparative tests.

The task for each panel member was to determine whether a given sample is less or more sweet than the reference solution. Each of the panel members completed a form according to the following rules: if a sample was sweeter, then he placed a plus sign [+] beside the symbol of the sample, if it was less sweet, a minus sign [−], and if in doubt, an equal sign [=]. Similar to the qualitative analysis, each of the panel members received a sample of 10 ml of a solution in a small vial, gently rinsed his mouth out with it for 20 seconds and then spat out the tested solution. Next, he carefully rinsed out his mouth with a large volume of distilled water (at least 150 ml) for at least 30 seconds. When the panel member felt that he no longer perceived any taste, he could proceed with the evaluation of the next solution.

All of the panel members declared beyond any doubt that the initial solution of the compound of example 1 is much sweeter than the reference solution (saccharose), which means that this compound is at least 50 times sweeter than saccharose.

The combined results of the quantification of 3-benzylaminomethylenedihydrofuran-2-oneu are shown in Table 2 below.

TABLE 2

| 3-benzylaminomethylene-dihydrofuran-2-one, content in solution, ppm | Results of sweetness comparisons against the reference solution [a, b, c] | | |
|---|---|---|---|
| | [+] | [=] | [−] |
| 4000 | 10 | | |
| 2000 | 10 | | |
| 1000 | 8 | | 2 |
| 800 | 2 | 6 | 2 |
| 500 | 2 | 2 | 6 |

[a] [+] denotes that the examined sample is sweeter than the reference solution,
[b] [−] denotes that the examined sample is less sweet than the reference solution,
[c] [=] denotes that the panel member was unable to tell which of the samples was sweeter.

A approximate interpretation of the results compiled in Table 2 yields the conclusion that 3-benzylaminomethylene-dihydrofuran-2-one is at least 200-250 times sweeter than saccharose, based on a comparison of a 10% saccharose solution in 20% ethanol.

Proceeding according to the above procedure, the study was repeated for the compound of example 2 ((R)-3-(1-phenylethylamino)methylenedihydrofuran-2-one). For this compound, the approximate interpretation of the results yields the conclusion that (R)-3-(1-phenylethylamino)methylenedihydrofuran-2-one is at least 200-250 times sweeter in comparison to a 10% saccharose solution in 20% ethanol.

The next study was performed on the compound of example 6 (2-benzylaminomethylenecyclopentanone). For this compound, the approximate interpretation of the results yields the conclusion that 2-benzylaminomethylene-cyclopentanone is at least 250 times sweeter in comparison to a 10% saccharose solution in 20% ethanol.

Inhibition of Sweet Taste

The inhibition of sweet taste of sweet substances or mixtures thereof by inhibitors of sweet taste according to the present invention was examine qualitatively according to the following procedure. Two samples of saccharose, each of 100 mg, are dissolved in 5 ml 20% of aqueous ethanol, and then one solution is supplemented with 100 mg of a compound of an example according to the present invention (compounds from examples 3, 5, and 8). Next, the taste of both solutions is evaluated using the procedure presented above, for the qualitative perception of a sweet taste. The study indicates that the saccharose solution with a compound of example 3 according to the present invention, or the compound of example 5, or the compound of example 8, is practically not sweet at all, in comparison to a saccharose solution without a compound according to the present invention. The results of the study show that the tested compounds according to the present invention: of example 3, example 5 and of example 8, exhibit inhibitory properties towards sweet taste. The study was also performed on compounds from comparative examples 1-19. The results are compiled in table 3.

TABLE 3

| Compound | Inhibition of sweet taste [a, b] |
|---|---|
| Example 3 according to the present invention | ++ |
| Example 5 according to the present invention | ++ |
| Example 8 according to the present invention | ++ |
| Comparative examples 1-19 | − |

[a] ++ complete inhibition of sweet taste,
[b] − lack of inhibition of sweet taste.

Solutions of sweet products were prepared (saccharose, glucose, bee honey, glycine), by dissolving 100 mg of the product in 5 ml 20% aqueous ethanol. Two solutions are prepared of each product. One of these solutions is supplemented with a compound according to example 3 of the present invention (100 mg). Next, the taste of both solutions is compared for evaluating the qualitative perception of the taste of both solutions, proceeding according to the procedure established above, for the qualitative evaluation of the perception of sweet taste. The study results are compiled in Table 4.

Solutions of commercially available sweeteners were prepared ("Sweet Top®" containing aspartame and L-leucine, "Sweet MagiC®" containing sorbitol, sodium cyclamate and sodium saccharinate), by dissolving 5 mg of the sweetener in 20 ml of 20% aqueous ethanol. Each sweetener solution was made up twice. One of these solutions was supplemented with a compound according to example 3 of the present invention (5 mg). Next, the taste of both solutions was evaluated proceeding according to the procedure shown above, for the qualitative evaluation of the perception of sweet taste. The study results are compiled in Table 4.

Solutions of compounds with a sweet taste according to the present invention were prepared (compounds of examples 1, 2 and 6), dissolving 5 mg of the compound according to the present invention in 20 ml 20% of aqueous ethanol. Two solutions were made of each compound of examples 1, 2 and 6. One of these solutions was supplemented with the compound of example 3 according to the present invention (5 mg). Next, the taste of both solutions was evaluated proceeding according to the above procedure for the qualitative evaluation of the perception of sweet taste. The study results are compiled in Table 4.

TABLE 4

Inhibition of sweet taste by (S)-3-(1-phenylethylamino)methylenedihydrofuran-2-one

| Sweet-tasting product (solution in 20% ethanol) | Perceived sweet taste[a] | Perception of sweet taste following the addition of the compound of example 3[b] |
|---|---|---|
| saccharose | ++ | <<+ |
| glucose | ++ | <<+ |
| bee honey | ++ | <<+ |
| glycine | ++ | <<+ |
| commercial sweetener Sweet Top ® (containing aspartame and L-leucine) | ++ | <<+ |
| commercial sweetener Sweet MagiC ® (containing sorbitol, sodium cyclamate and sodium saccharinate) | ++ | <<+ |
| 3-benzylaminomethylenedihydrofuran-2-one (compound of example 1) | ++ | <<+ |
| (R)-3-(1-phenylethylamino)methylene-dihydrofuran-2-one (compound of example 2) | ++ | <<+ |
| 2-benzylaminomethylenecyclopentanone (compound of example 6) | ++ | <<+ |

[a] ++ Strong perception of sweet taste,
[b] <<+ Weak or absent perception of sweet taste.

Solutions of saccharose, glucose, bee honey or glycine with an addition of the compound of example 3, do not elicit the perception of a sweet taste, not even a weak one. For solutions of sweeteners such as Sweet Top® or Sweet MagiC®, the solutions of which at the given concentration are very sweet, the addition of the compound of example 3 results in a very significant decrease in the perception of sweetness. The solution of example 2 with an addition of example 3 does not exhibit a sweet taste. A solution of the compound of example 1 with an addition of a compound of example 3 exhibits only a trace perceived sweet taste, similar to the compound of example 6 with an addition of the compound of example 3.

Compounds with the formula I according to the present invention, can be used to manufacture products in various forms and intended uses, for example in products in the form of a powder, tablets, syrups, suspensions, preparations for chewing or sucking, for the modification of foodstuffs, cosmetics and pharmaceuticals. They are designed to be used separately, but also in combination with other natural or synthetic taste modifiers. Sweeteners according to the present invention can be used in combination with other known sweeteners in order to improve their taste, and/or to elicit a synergistic effect. Inhibitors of sweet taste according to the present invention (which lack taste as individual compounds) are meant for the modification of the taste of such products as are perceived to be excessively sweet. The inhibitors are meant for use alone and in combination with other known natural or synthetic inhibitors of sweet taste. They may also be used in mixtures with other known sweeteners to improve their taste.

The invention claimed is:

1. A composition comprising a compound having the structure of formula I

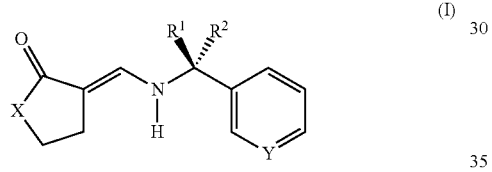

in which
X denotes O or $CH_2$,
Y denotes N and each of $R^1$ and $R^2$ denotes hydrogen,
or Y denotes a CH, either $R^1$ or $R^2$ denotes a $C_{1-4}$ alkyl, and the remaining $R^1$ or $R^2$ denotes hydrogen,
wherein if Y denotes CH, and at the same time $R^1$ or $R^2$ denotes a $C_{1-4}$ alkyl, then the composition comprises
(i) a mixture of R and S enantiomers of the compound enriched in enantiomer R,
(ii) a mixture of R and S enantiomers of the compound enriched in enantiomer S,
(iii) R enantiomers of the compound free of S enantiomers or
(iv) S enantiomers of the compound free of R enantiomers, and
wherein the compound is in the form of isomer E, and/or isomer Z, and/or a tautomer.

2. The composition according to claim 1, wherein X denotes O or $CH_2$, Y denotes a CH, either $R^1$ or $R^2$ denotes a $C_{1-4}$ alkyl, and the remaining $R^1$ or $R^2$ denotes hydrogen, and wherein the composition co rises
(i) a mixture of R and S enantiomers of the compound containing at least 90% enantiomer R,
(ii) a mixture of R and S enantiomers of the compound containing at least 90% enantiomer S,
(iii) R enantiomers of the compound free of S enantiomers or
(iv) S enantiomers of the compound free of R entantiomers, and
wherein the compound is in the form of isomer E, and/or isomer Z and/or a tautomer.

3. The composition according to claim 1, wherein X denotes O or $CH_2$, Y denotes a CH, either $R^1$ or $R^2$ is methyl or ethyl, and the remaining $R^1$ or $R^2$ denotes hydrogen.

4. The composition according to claim 3, wherein the compound is (R)-3-(1-phenylethyl)aminomethylenedihydrofuran-2-one.

5. The composition according to claim 3, wherein the compound is
(S)-3-(1-phenylethyl)aminomethylenedihydrofuran-2-one,
(R)-3-(1-phenylpropyl)aminomethylenedihydrofuran-2-one,
(S)-3-(1-phenylpropyl)aminomethylenedihydrofuran-2-one,
(R)-2-(1-phenylethyl)aminomethylenecyclopentanone, or
(S)-2-(1-phenylethyl)aminomethylenecyclopentanone.

6. The composition according to claim 1, wherein the compound is 3-(3-pyridylmethyl)aminomethylenedihydrofuran-2-one.

7. A method for modifying the sweetness of a product comprising
combining the product with a composition comprising a compound having the structure of formula I so as to modify the sweetness of the product

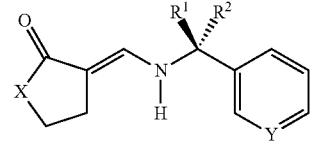

wherein
X denotes O or $CH_2$, Y denotes a CH, either $R^1$ or $R^2$ is hydrogen or a $C_{1-4}$ alkyl, and the remaining $R^1$ or $R^2$ denotes hydrogen, wherein if $R^1$ or $R^2$ denotes a $C_{1-4}$ alkyl, the composition comprises
(i) a mixture of R and S enantiomers of the compound enriched in enantiomer R,
(ii) a mixture of R and S enantiomers of the compound enriched in enantiomer S,
(iii) R enantiomers of the compound free of S enantiomers or
(iv) S enantiomers of the compound free of R enantiomers, wherein the compound is in the form of isomer E, and/or isomer Z and/or a tautomer;
and wherein the product is a foodstuff, cosmetic, pharmaceutical, toothpaste, chewing gum, or mouthwash.

8. The method according to claim 7, wherein R1 and R2 are hydrogen and the composition imparts sweetness or enhances the perception of sweetness of the product.

9. The method according to claim 8, wherein the compound is 3-benzylaminomethylenedihydrofuran-2-one or 2-benzylaminomethylenecyclopentanone.

10. The method according to claim 7, wherein $R^1$ or $R^2$ denotes a $C_{1-4}$ alkyl, and the remaining $R^1$ or $R^2$ denotes hydrogen, and the composition comprises (i) a mixture of R and S enantiomers of the compound enriched in enantiomer R or (ii) R enantiomers of the compound free of S enantiomers.

11. The method according to claim 10, wherein the compound is (R)-3-(1-phenylethyl)aminomethylenedihydrofuran-2-one.

12. The method according to claim 10, wherein the compound is (R)-3-(1-phenylpropyl)aminomethylenedihydrofuran-2-one or (R)-2-(1-phenylethyl)aminomethylenecyclopentanone.

13. The method according to claim 7, wherein either $R^1$ or $R^2$ denotes a $C_{1-4}$ alkyl, and the remaining $R^1$ or $R^2$ denotes hydrogen, and the composition comprises (i) a mixture of R and S enantiomers of the compound enriched in enantiomer S or (ii) S enantiomers of the compound free of R enantiomers, and the composition inhibits the perception of sweetness of the product.

14. The method according to claim 13, wherein the compound is
- (S)-3-(1-phenylethyl)aminomethylenedihydrofuran-2-one,
- (S)-3-(1-phenylpropyl)aminomethylenedihydrofuran-2-one, or
- (S)-2-(1-phenylethyl)aminomethylenecyclopentanone.

15. A composition
  which is a foodstuff, cosmetic, pharmaceutical, toothpaste, chewing gum, or mouthwash
  comprising the compound of claim 1.

16. The composition of claim 15, wherein X denotes O or $CH_2$, Y denotes a CH, either $R^1$ or $R^2$ denotes a $C_{1-4}$ alkyl, and the remaining $R^1$ or $R^2$ denotes hydrogen, and wherein the composition comprises
  (i) a mixture of R and S enantiomers of the compound containing at least 90% enantiomer R,
  (ii) a mixture of R and S enantiomers of the compound containing at least 90% enantiomer S,
  (iii) R enantiomers of the compound free of S enantiomers or
  (iv) S enantiomers of the compound free of R enantiomers, and
wherein the compound is in the form of isomer E, and/or isomer Z and/or a tautomer.

17. The composition of claim 15, wherein X denotes O or $CH_2$, Y denotes a CH, either $R^1$ or $R^2$ is methyl or ethyl, and the remaining $R^1$ or $R^2$ denotes hydrogen.

18. The composition of claim 15, wherein the compound is (R)-3-(1-phenylethyl)aminomethylenedihydrofuran-2-one.

19. The composition of claim 15, wherein the compound is
- (S)-3-(1-phenylethyl)aminomethylenedihydrofuran-2-one,
- (R)-3-(1-phenylpropyl)aminomethylenedihydrofuran-2-one,
- (S)-3-(1-phenylpropyl)aminomethylenedihydrofuran-2-one,
- (R)-2-(1-phenylethyl)aminomethylenecyclopentanone, or
- (S)-2-(1-phenylethyl)aminomethylenecyclopentanone.

20. The composition of claim 15, wherein the compound is 3-(3-pyridylmethyl)aminomethylenedihydrofuran-2-one.

* * * * *